US011795523B2

(12) United States Patent
Bitton (10) Patent No.: US 11,795,523 B2
(45) Date of Patent: *Oct. 24, 2023

(54) METHOD AND SYSTEM FOR IMPROVING WASTE METAL BATCH COMPOSITION

(71) Applicant: House of Metals Company Limited, Toronto (CA)

(72) Inventor: Daniel Bitton, Toronto (CA)

(73) Assignee: HOUSE OF METALS COMPANY LIMITED, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/723,556

(22) Filed: Apr. 19, 2022

(65) Prior Publication Data

US 2022/0235432 A1  Jul. 28, 2022

Related U.S. Application Data

(63) Continuation of application No. 16/780,163, filed on Feb. 3, 2020, now Pat. No. 11,332,807.

(Continued)

(51) Int. Cl.
*C22B 7/00* (2006.01)
*B24C 3/32* (2006.01)
(Continued)

(52) U.S. Cl.
CPC ............... *C22B 7/005* (2013.01); *B24C 3/32* (2013.01); *C22B 21/0069* (2013.01); *G01J 3/50* (2013.01)

(58) Field of Classification Search
None
See application file for complete search history.

(56) References Cited

U.S. PATENT DOCUMENTS

| 3,905,556 A | 9/1975 | Drage |
| 4,069,145 A | 1/1978 | Sommer, Jr. et al. |

(Continued)

FOREIGN PATENT DOCUMENTS

| CA | 1110996 | 10/1981 |
| JP | 02083167 | 3/1990 |

(Continued)

OTHER PUBLICATIONS

Search Report and Written Opinion dated May 7, 2020, in respect of PCT/CA2020/050125.

(Continued)

*Primary Examiner* — Scott R Kastler
(74) *Attorney, Agent, or Firm* — Bereskin & Parr LLP/S.E.N.C.R.L., s.r.l.

(57) ABSTRACT

Described herein is a method for recycling aluminum alloy wheels. The method includes the steps of providing a feed of aluminum alloy wheels of a particular alloy; fragmenting a quantity of the aluminum alloy wheels into a plurality of fragments; subjecting the plurality of fragments to shot blasting to remove surface impurities from the plurality of fragments to produce a plurality of shot blasted pieces; separating the plurality of shot blasted pieces into a plurality of larger shot blasted pieces and a plurality of smaller shot blasted pieces; and, providing the plurality of larger shot blasted pieces for use in producing a recycled aluminum alloy, without providing the plurality of smaller shot blasted pieces for use in producing that recycled aluminum alloy.

17 Claims, 7 Drawing Sheets

Related U.S. Application Data (60) Provisional application No. 62/871,784, filed on Jul. 9, 2019.

(51) Int. Cl.
    *G01J 3/50* (2006.01)
    *C22B 21/00* (2006.01)

(56) References Cited

U.S. PATENT DOCUMENTS

| | | |
|---|---|---|
| 4,136,778 A | 1/1979 | Wortman et al. |
| 4,337,900 A | 7/1982 | Williams et al. |
| 4,476,655 A | 10/1984 | Ansbaugh |
| 4,609,155 A | 9/1986 | Garnier |
| 4,848,590 A | 7/1989 | Kelly |
| 4,965,968 A | 10/1990 | Kelsall |
| 5,060,871 A | 10/1991 | Brassinga et al. |
| 5,133,505 A | 7/1992 | Bourcier et al. |
| 5,314,072 A | 5/1994 | Frankel et al. |
| 5,333,797 A | 8/1994 | Becker et al. |
| 5,443,157 A | 8/1995 | Baker et al. |
| 5,663,997 A | 9/1997 | Willis et al. |
| 5,738,224 A | 4/1998 | Sommer, Jr. et al. |
| 5,769,331 A | 6/1998 | Yamagishi et al. |
| 5,885,141 A | 3/1999 | Watkin |
| 6,375,106 B1 | 4/2002 | Sears |
| 6,422,493 B1 | 7/2002 | Simon et al. |
| 6,527,206 B1 | 3/2003 | Wuebbels et al. |
| 6,983,901 B2 | 1/2006 | Bitton et al. |
| 8,322,639 B2 | 12/2012 | Gitschel |
| 9,086,618 B2 | 7/2015 | Suga |
| 9,475,652 B2 | 10/2016 | Nichols et al. |
| 10,207,296 B2 | 2/2019 | Garcia et al. |
| 10,220,418 B2 | 3/2019 | Bitton |
| 11,332,807 B2 * | 5/2022 | Bitton ................ C22B 21/0069 |
| 2005/0051645 A1 | 3/2005 | Bitton et al. |
| 2005/0051647 A1 | 3/2005 | Bitton et al. |
| 2017/0173636 A1 | 6/2017 | Bitton |
| 2018/0147607 A1* | 5/2018 | Comtois ................ B07C 5/344 |
| 2018/0229274 A1 | 8/2018 | Kurth et al. |
| 2019/0134672 A1 | 5/2019 | Bitton |

FOREIGN PATENT DOCUMENTS

| | | |
|---|---|---|
| JP | 02160473 | 6/1990 |
| WO | 9519454 | 7/1995 |

OTHER PUBLICATIONS

Office Action dated Apr. 29, 2021 in respect of U.S. Appl. No. 16/780,163.

Office Action dated Jul. 20, 2021 in respect of U.S. Appl. No. 16/780,163.

European Search Report dated Jun. 1, 2023 in respect of European Application No. 20837244.1.

* cited by examiner

METHOD AND SYSTEM FOR IMPROVING WASTE METAL BATCH COMPOSITION

CROSS REFERENCE TO RELATED APPLICATIONS

This application is a continuation of U.S. application Ser. No. 16/780,163 filed Feb. 3, 2020, now U.S. Pat. No. 11,332,807 issued on May 17, 2022, which claims the benefit of U.S. Provisional Application No. 62/871,784 filed Jul. 9, 2019, the entirety of which are hereby incorporated by reference.

FIELD

The described embodiments relate to the field of recycling, in particular, the field of recycling waste metal and improving the composition of a batch of recyclable waste metal.

BACKGROUND

Recycling what would otherwise be waste materials to form new materials or objects is important in modern waste management. Many different materials can be recycled, for example, glass, paper, cardboard, metal, plastic, tires, textiles, batteries, and electronics. The typical method for recycling waste material includes pickup, sorting, cleaning, and processing.

Metals are of particular value for recycling. Unlike other materials, metals may be recycled into products of substantially similar quality to their feed material.

When using recycled metals as a feed stock for the manufacture of metal products, it is important to know, or at least have reasonably accurate estimates of, the composition of this feedstock. Slight differences in elemental composition can result in vastly different material properties. Certain high value alloys have very specific elemental compositions. Accurately measuring and controlling elemental composition can increase the value extracted from waste materials.

SUMMARY

This summary is intended to introduce the reader to various aspects of the applicant's teaching, but not to define any specific embodiments. In general, disclosed herein are one or more methods recycling waste metal.

In a first aspect, some embodiments of the invention provide a method of recycling aluminum alloy wheels. The method comprises: providing a feed of aluminum alloy wheels of a particular alloy; fragmenting a quantity of the aluminum alloy wheels into a plurality of fragments; subjecting the plurality of fragments to shot blasting to remove surface impurities from the plurality of fragments to produce a plurality of shot blasted pieces; separating the plurality of shot blasted pieces into a plurality of larger shot blasted pieces and a plurality of smaller shot blasted pieces; and, estimating a composition of the plurality of larger shot blasted pieces by selecting multiple shot blasted pieces from the plurality of smaller shot blasted pieces and then measuring the composition of the multiple shot blasted pieces.

According to some aspects of some embodiments of the present invention subjecting the pieces to shot blasting comprises producing most of the plurality of smaller shot blasted pieces.

According to some aspects of some embodiments of the present invention producing most of the plurality of smaller shot blasted pieces comprises shot blasting the plurality of fragments to break most of the plurality of smaller shot blasted pieces off the plurality of fragments.

According to some aspects of some embodiments of the present invention providing the larger shot blasted pieces, and the composition of the plurality of larger shot blasted pieces, for use in manufacturing a component made from aluminum alloy. In some aspects of some embodiments, the component may be an aluminum alloy wheel. In some aspects of some embodiments, the aluminum alloy may be A356.2 aluminum alloy. In some aspects of some embodiments, collecting the smaller shot blasted pieces for use in producing a product different from the component made from the larger shot blasted pieces.

According to some aspects of some embodiments of the present invention, separating the plurality of shot blasted pieces into the plurality of larger shot blasted pieces and the plurality of smaller shot blasted pieces comprises passing the plurality of smaller shot blasted pieces through a plurality of holes, the plurality of larger shot blasted pieces being too large to pass through the plurality of holes. In some aspects of some embodiments, a threshold maximum breadth of each hole in the plurality of holes may be between half an inch and one inch.

According to some aspects of some embodiments of the present invention, more than 95% of a mass of the quantity of the aluminum alloy wheels may be fragmented into fragments larger than the plurality of smaller shot blasted pieces.

According to some aspects of some embodiments of the present invention, more than 99% of a mass of the quantity of the aluminum alloy wheels is fragmented into fragments having a maximum length of greater than 1 inch.

According to some aspects of some embodiments of the present invention, more than 99% of a mass of the quantity of the aluminum alloy wheels is fragmented into fragments having a maximum length of between 1 inch and 8 inches.

According to some aspects of some embodiments of the present invention, measuring the composition of the multiple shot blasted pieces comprises: melting the smaller shot blasted pieces to produce a homogeneous aggregate; heating a material of that homogeneous aggregate in at least one spot on a surface of the homogeneous aggregate to a point where the material of that homogeneous aggregate will emit a characteristic radiation while cooling down; detecting the characteristic radiation emitted by the material of that homogeneous aggregate; and, operating a processor to analyze that characteristic radiation to determine the composition of the material of that homogeneous aggregate.

According to some aspects of some embodiments of the present invention, measuring the composition of the multiple shot blasted pieces comprises using laser spectroscopy.

According to some aspects of some embodiments of the present invention, measuring the composition of the multiple shot blasted pieces comprises, for each piece of the multiple shot blasted pieces, i) heating a material of that shot blasted piece in at least one spot on a test surface of the shot blasted piece to a point where the material of that shot blasted piece will emit a characteristic radiation while cooling down; ii) detecting the characteristic radiation emitted by the material of that shot blasted piece; and iii) operating a processor to analyze that characteristic radiation to determine the composition of the material of that shot blasted piece. For each piece of the multiple shot blasted pieces, the method may further comprise providing the test surface of the shot blasted piece by removing layers of aluminum formerly covering the test surface to expose the test surface.

According to some embodiments of the present invention, there is provided a system for recycling aluminum alloy wheels. The system comprises a conveyor for providing a feed of aluminum alloy wheels of a particular alloy; a fragmenting unit for receiving the feed of aluminum alloy wheels from the conveyor and for fragmenting the aluminum alloy wheels into a plurality of fragments; a blast chamber for receiving the plurality of fragments from the fragmenting apparatus and for subjecting the plurality of fragments to shot blasting to provide a plurality of shot blasted pieces; a separator for receiving the plurality of shot blasted pieces and for separating the plurality of shot blasted pieces into a plurality of larger shot blasted pieces and a plurality of smaller shot blasted pieces; and, a processor/analyzer for determining an aggregate composition of multiple shot blasted pieces selected from the plurality of smaller shot blasted pieces.

In some variants of the system for recycling aluminum alloy wheels, the processor/analyzer comprises a laser for heating a material of the multiple shot blasted pieces to a point where the material of the multiple shot blasted pieces will emit a characteristic radiation while cooling down; a sensor for detecting the characteristic radiation emitted by the material of the multiple shot blasted pieces; and, a processor for analyzing that characteristic radiation to determine the aggregate composition of multiple shot blasted pieces.

In some variants of the system for recycling aluminum alloy wheels, the separator comprises a separation barrier comprising a plurality of holes; in operation, the separator urges the plurality of shot blasted pieces against a first side of the separation barrier and the plurality of holes; and, the plurality of smaller shot blasted pieces are dimensioned to pass the plurality of smaller shot blasted pieces through to an opposite side of the separation barrier, and to retain the plurality of larger shot blasted pieces on the first side of the separation barrier. The threshold maximum breadth of each hole in the plurality of holes can be between half an inch and one inch.

In some variants of the system for recycling aluminum alloy wheels, the fragmenting unit comprises a plurality of shredders or cutters configured such that, in operation, more than 95% of a mass of the plurality of fragments is contained within fragments too large to pass through the plurality of holes.

In some variants of the system for recycling aluminum alloy wheels, the fragmenting unit comprises a plurality of shredders or cutters configured such that, in operation, more than 99% of a mass of the plurality of fragments is contained within fragments too large to pass through the plurality of holes.

In some variants of the system for recycling aluminum alloy wheels, the processor/analyzer comprises a melting receptacle for melting and mixing the multiple smaller shot blasted pieces to produce an homogeneous aggregate; a laser for heating a material of that homogeneous aggregate in at least one spot on a surface of the homogeneous aggregate to a point where the material of that homogeneous aggregate will emit a characteristic radiation while cooling down; a sensor for determining the characteristic radiation emitted by the material of that homogeneous aggregate; and, a processor for analyzing that characteristic radiation to determine the composition of the material of that homogeneous aggregate.

BRIEF DESCRIPTION OF THE DRAWINGS

These and other advantages of the instant invention will be more fully and completely understood in conjunction with the following detailed description of embodiments and aspects of the present invention with reference to the following drawings, in which.

DESCRIPTION OF EXEMPLARY EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

Figure 1:
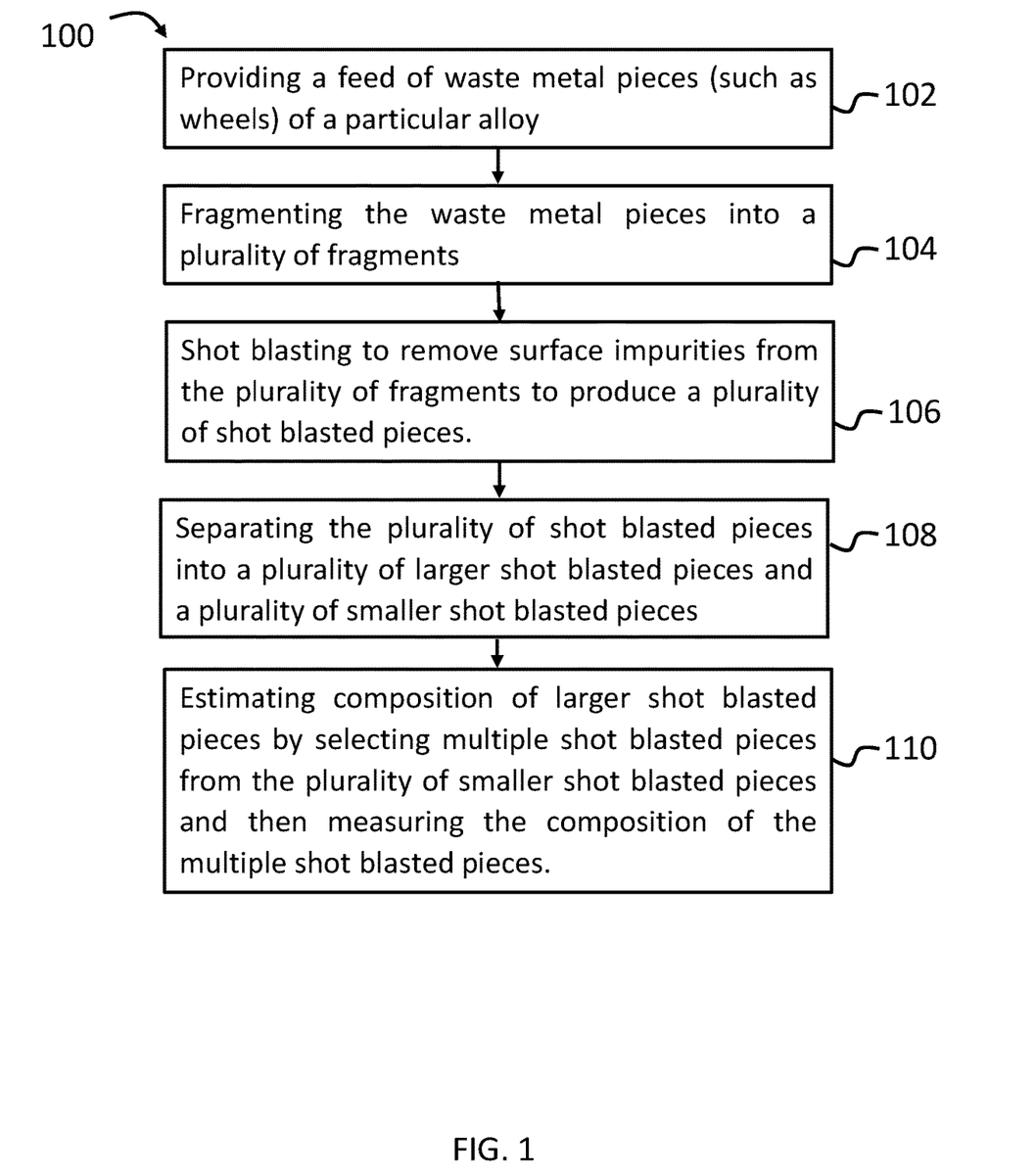
FIG. 1, in a flow chart, illustrates a method for estimating a batch composition of a feed of waste metal pieces.

Reference is first made to FIG. 1, in which a method 100 for estimating a batch composition of a feed of waste metal pieces is shown. Method 100 begins with providing a feed of waste metal pieces 102. The waste metal pieces provided at step 102 are of a particular alloy type. For example, the feed of waste metal pieces may be a feed of waste metal pieces composed of aluminum alloys. In other examples, the feed of waste metal pieces may be a feed of waste metal pieces composed of any one of bismuth alloys, brass alloys, cobalt alloys, copper alloys, gallium alloys, gold alloys, indium alloys, iron alloys, lead alloys, magnesium alloys, mercury alloys, nickel alloys, potassium alloys, silver alloys, steel alloys, tin alloys, titanium alloys, zinc alloys, zirconium alloys, etc.

In some examples of method 100, although each piece of waste metal in the feed may be made of the same alloy type, its composition may differ from the composition of at least one of the other pieces in the feed. In some examples, a piece may be one composition of two different compositions present in the feed. In other examples, a piece of waste metal may have one composition of any number of different compositions present in the feed of waste metal. The batch of waste metal pieces has an aggregate or batch composition based on the different compositions of the different pieces of waste metal, as well as the relative masses of those pieces of waste metal. For example, if all pieces of waste metal were to be melted down and mixed to provide a homogeneous aggregate or mixture, then this aggregate or batch composition would have the composition of that homogeneous mixture. This batch composition of the feed of waste metal pieces may be unknown when the pieces of waste metal are initially provided.

This feed of waste metal may all originate from the same kind of components being recycled. For example, a feed of aluminum alloy wheels of a particular alloy, such as aluminum alloy A356.2. Despite all the wheels being of a particular alloy type, they may nonetheless differ slightly in composition. Material properties may vary significantly with slight variations in composition. Alloys with certain specific elemental compositions may result in material properties that are much more desirable than alloys with slightly varying elemental compositions. These material properties may include mechanical strength properties, chemical resistance properties, corrosion resistance and other properties. For example, certain specific elemental compositions may result in a measurably greater mechanical yield strength in tension.

At step 104, the waste metal pieces are fragmented into a plurality of fragments. In some examples, fragments may be produced by passing waste metal pieces through a fragmenting unit. A fragmenting unit may be a shredding apparatus. Any suitable shredder known in the art may be used. For example, waste metal pieces may be supplied to a hopper of a conventional shredding apparatus, such as the SSI Series 45H shredder available from SSI Shredding Systems Inc. at 9760 SW Freeman Drive, Wilsonville, Oreg., 97070-9286, USA. This shredding apparatus may include a cutter box housing cutters, which can be mounted on parallel shafts that rotate horizontally in opposite directions. The feed hopper can be located above the cutter box. Due to the force of gravity, the rims placed in the feed hopper can then be fed downwardly into the proper location where they can be engaged by the cutters and torn or cut into shreds.

At step 106, fragments are subjected to shot blasting. Waste metal pieces provided at step 102 may be coated in a number of coatings, such as paints, metal electroplating, ceramic coatings or plastic coatings. Similarly, external surfaces of waste metal pieces may be characterized by corrosion or environmental contamination. After fragmenting process 104, surfaces of fragments that were previously external surfaces of waste metal pieces may still be coated with a coating, corroded or otherwise contaminated. Newly exposed surfaces created by fragmenting process 104 may be devoid of coatings.

When waste metal pieces or fragments created from the waste metal pieces are provided for recycling, the recycling process may include melting pieces into a bulk or aggregate batch. The composition of the aggregate batch would include elements present in any coatings or surface contamination present on the external surfaces of provided waste metal pieces, skewing the aggregate batch composition away from the composition of base alloys provided. This is undesirable, as material properties are sensitive to elemental composition. It is desirable to remove external surface coatings, corrosion and surface contamination, leaving behind a bare metal surface, free of contamination, coatings or corrosion.

During the shot blasting process 106, abrasive particles can be projected at the fragments at high speed. Abrasives impact the surfaces of the fragments. These impacts can dislodge coatings, corrosion, contamination and debris deposited on the surface of the fragments, resulting in fragments with bare metal surfaces largely free from coatings, corrosion, environmental contamination and debris.

Shot blasting may be conducted in any suitable shot blasting apparatus. For example, the apparatus may be a centrifugal blasting apparatus, such as the model (FB-4/28/E/MR) Flexbel system available from BCP Wheelabrator of 1219 Corporate Drive, Burlington, Ontario, L7L 5V5, Canada, which is suitable for blast cleaning small parts. Abrasives may include steel shot, alumina, silica and other abrasive materials, of any size. Preferably, one half inch or larger S330 steel shot, also available from BCP Wheelabrator, can be used.

At step 106, abrasives may impact fragments with sufficiently high energy such that singular fragments are separated into multiple shot blasted pieces. In some examples, fragments may be separated into shot blasted pieces that are of substantially the same mass. For example, a single fragment may be separated into two shot blasted pieces during the shot blasting process. These two pieces may each be approximately half the mass of the fragment that the shot blasted pieces were formed from. In other examples, a single fragment may be separated into two pieces, wherein one piece is substantially the same mass as the fragment that the shot blasted pieces were formed from, and the other piece is of a significantly smaller mass. In other examples, a single fragment may be separated into a plurality of pieces, of varying masses. In some embodiments, step 106 can produce shot blasted pieces much smaller than any fragment in the plurality of fragments produced in step 104.

At step 106, some fragments may be impacted with abrasives, yet remain intact. For example, a single fragment may be impacted with abrasives during the shot blasting process. Only a single shot blasted piece is produced during this operation. The resulting shot blasted piece produced is substantially the same mass as the fragment that produced the shot blasted piece. Any discrepancy in mass may be attributed to the removal of any surface coatings, corrosion, contamination and debris, present on the surface of the fragment before the shot blasting operation, in addition to the absence of a relatively thin layer of base metal material that may have been removed during the shot blasting operation.

Additional steps may be performed after shot blasting process 106 to remove abrasive particles and debris produced during the shot blasting process. These steps may include washing or rinsing with a pressurized fluid, such as air, water or mineral oil to clear abrasive particles and debris from shot blasted pieces, or sifting or vibrating the shot blasted parts on a screen, mesh or grate, or, when the shot is made of a suitable material such as steel, using a magnet to draw the shot out of the shot blasted pieces.

At step 108, a plurality of shot blasted pieces are divided to provide a plurality of larger shot blasted pieces and a plurality of smaller shot blasted pieces. The fragmentation process at step 104 may produce fragments of various sizes. Similarly, the shot blasting process at step 106 may further separate fragments of various sizes into shot blasted pieces of various sizes. At step 108, a feed of shot blasted pieces is provided, with shot blasted pieces of varying sizes. This feed of shot blasted pieces is separated into two distinct groups, one group of smaller shot blasted pieces and another group of larger shot blasted pieces. Separation may be conducted using any number of methods known in the art.

At step 110, multiple shot blasted pieces are selected from the plurality of smaller shot blasted pieces. The composition of the multiple smaller shot blasted pieces is measured or estimated. Any method known in the art to determine composition of a material sample may be used to determine or estimate composition.

Using the measured or estimated composition of the selection of smaller shot blasted pieces, the composition of the larger shot blasted pieces can be estimated, since the smaller shot blasted pieces derive from the same material feed as the larger shot blasted pieces, at step 102 in which the feed of waste metal pieces are provided.

When measuring composition, samples may be melted into an aggregate sample to effectively average the composition of many samples of varying origin, providing a more representative material sample for testing. Additionally, due to a number of metallurgical effects, surface composition of metallic samples may differ from internal composition. These effects include oxidation and element migration.

For a number of reasons, it can be advantageous to estimate or measure the composition of the smaller shot blasted pieces. The composition of the smaller shot blasted pieces are likely to be representative of the composition of the larger shot blasted pieces, as they originate from the same feed of waste metal pieces. Smaller shot blasted pieces may require less time and energy to melt into an aggregate sample. Additionally, smaller shot blasted pieces may be of lower value, as smaller shot blasted pieces are likely to have a larger surface area relative to their mass, increasing the impurities or dross at risk of being included in the recycled aluminum alloy, thereby potentially reducing the value of the recycled aluminum. By using smaller shot blasted pieces to estimate the composition of larger shot blasted pieces, larger shot blasted pieces need not be used to estimate composition. Instead of using large amounts of energy to melt down high value, larger shot blasted pieces into an aggregate sample for testing, smaller, low value, shot blasted pieces may be melted down into an aggregate sample, using less energy, to obtain an estimate of large shot blasted piece composition. Larger shot blasted pieces can then be provided in their unprocessed form to be recycled into different metal components using the composition estimate obtained by processing the smaller shot blasted pieces.

In some examples, compositions of smaller shot blasted pieces may not be representative of the composition of the larger shot blasted pieces. Due to variations in composition of fragments produced at step 104, some fragments may have compositions that are more likely to result in smaller shot blasted pieces being produced during the shot blasting process 106. The fragments may be more brittle, and therefor prone to shattering into smaller pieces on impact. Other fragments may have a material composition that results in a less brittle fragments, which are less likely to result in the creation of smaller shot blasted pieces during the shot blasting process 106. To compensate for this possible variation, composition measurements can be taken from multiple smaller shot blasted pieces.

In some examples, a correction factor may be applied when deriving an estimate of the composition of the larger shot blasted pieces from the estimate of the composition of the multiple smaller shot blasted pieces. For example, if it is known a priori what proportion of the plurality of fragments are likely to be brittle and thus to break into smaller pieces during shot blasting step 106, and how this will affect the composition estimate of the multiple smaller shot blasted pieces, since the relatively brittle fragments are more likely to provide these smaller shot blasted pieces then their relative proportion within the plurality of fragments would otherwise suggest, then a correction factor can be applied to counteract this effect. For example, if the relatively brittle fragments are likely to have a higher composition of some elements and a lower composition of others, then the estimate of the composition of the multiple smaller shot blasted pieces is likely to reflect these higher and lower composition measurements in predictable ways, especially where many smaller shot blasted pieces are used to determine the estimate of the composition of the multiple smaller shot blasted pieces. The correction factor can then be used to adjust these higher and lower composition measurements to compensate for the overrepresentation of the brittle fragments in the multiple smaller shot blasted pieces.

Using statistical methods, the composition of the larger shot blasted pieces can be estimated using known input qualities, such as composition of the selection of smaller shot blasted pieces, sampling method and sample specifications. The certainty of this estimate can also be estimated using known statistical sampling and testing methods. Any statistical method known in the art to provide an estimate of an attribute of a population, from a smaller sample may be used to provide composition estimation of the larger shot blasted pieces.

Method 100 can provide a feed of larger shot blasted pieces, with an estimate of composition of these pieces. The composition estimate may include uncertainty data. This feed of shot blasted pieces, along with the composition estimate, can be provided to a recycling facility, such as a foundry, for incorporation into a recycling process in order to recycle the larger shot blasted pieces into new metal products. The composition estimate may be used to determine what products the shot blasted pieces may be recycled into, or what other aluminum alloy materials, and in what quantities, the larger shot blasted pieces can be mixed with to provide target aluminum alloy. Providing the composition estimate with the larger shot blasted pieces can increase the value of the larger shot blasted pieces, by allowing recycling facilities to incorporate these larger shot blasted pieces into more valuable aluminum alloy batches.

Figure 2:
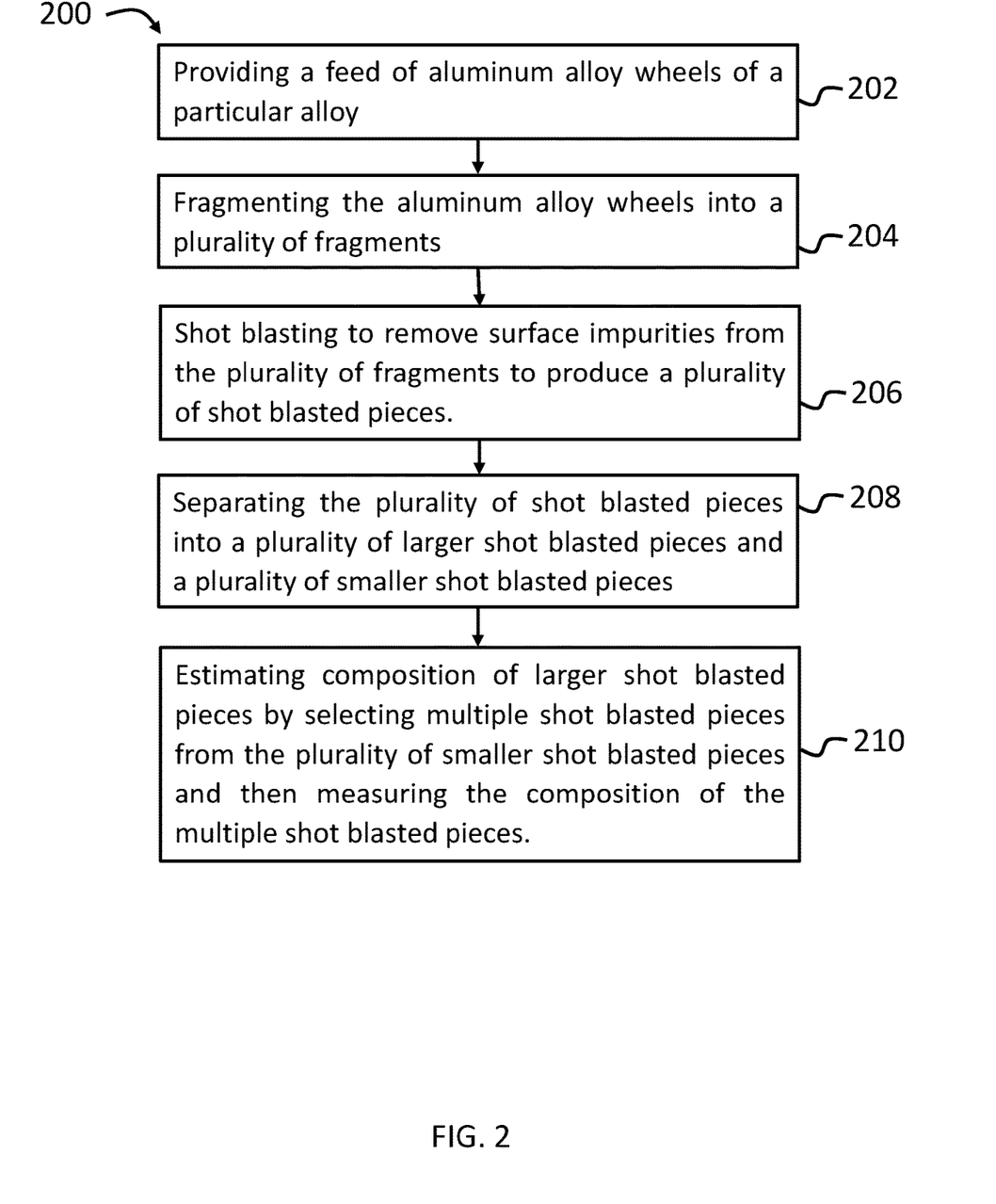
FIG. 2, in a flow chart, illustrates a method of estimating a batch composition of a feed of aluminum alloy wheels for recycling.

Referring now to FIG. 2, shown therein is method 200 of recycling aluminum alloy wheels. Method 200 of recycling aluminum alloy wheels is an example of an application of method 100 of determining a batch composition of a feed of waste metal pieces. Accordingly, any of the examples discussed below may be applied to method 100 and any examples discussed above in reference to method 100 can be applied to method 200. Moreover, the discussion below is not meant to limit the methods described herein to that of recycling aluminum alloy wheels. For example, the methods described herein may be applied to a method for recycling objects made of steel alloys, copper alloys, or any other suitable metal.

In step 202 of method 200, a feed of aluminum alloy wheels of a particular alloy is provided. In some examples, this alloy may be A356.2 aluminum alloy. Similar to the waste metal products described above, although the aluminum alloy wheels are of a particular alloy, the composition of the wheels may vary. Accordingly, the aggregate composition of a batch of aluminum alloy wheels may be unknown when the batch is initially provided.

In step 204 of method 200, the aluminum alloy wheels are fragmented into a plurality of fragments. The wheels may be fragmented by running wheels through a fragmenting unit, such as an industrial shredder. Fragments produced by the fragmenting process may be of substantially uniform size.

The size of fragments produced during the fragmenting process 204 will vary depending on the design and configuration of the fragmenting unit, for example, the size and orientation of shredders or cutters. The fragments may be just small enough to facilitate removal of contaminants. Put another way, the fragments may be as large as possible given the need to remove the contaminants. They may, for example, be much larger than the smaller shot blasted pieces produced in step 208.

In some examples, more than 95% of the mass of fragments produced in step 204 may be larger than the plurality of smaller shot blasted pieces produced in step 208.

In some examples, more than 99% of the mass of fragments produced in step 204 may be larger than the plurality of smaller shot blasted pieces produced in step 208.

In some examples, more than 99% of the mass of fragments produced in step 204 may have a maximum length greater than 1 inch.

In some examples, more than 99% of the mass of fragments produced in step 204 may have a maximum length between 1 inch and 8 inches.

In step 206 of method 200, fragments are subjected to shot blasting. Abrasive particles are directed at the fragments at high speed. These particles impact the surface of the fragments, dislodging coatings, corrosion, and environmental contamination. The resulting shot blasted pieces can be bare, aluminum alloy shot blasted pieces.

In step 206 of method 200, abrasives may impact fragments with sufficiently high energy to separate singular fragments into a plurality of shot blasted pieces, which are smaller than the fragments that they are produced from.

In step 208 of method 200, the shot blasted pieces are separated into a plurality of larger shot blasted pieces and smaller shot blasted pieces. In some examples of method 200, the majority of smaller shot blasted pieces may be produced during the shot blasting process 206, by abrasives impacting larger fragments with sufficiently high energy to separate singular fragments into a plurality of shot blasted pieces of various sizes. Some of these shot blasted pieces may be much smaller than almost all of the fragments produced in step 204, as small shot blasted pieces can be chipped off much larger fragments during step 206.

Figure 3:
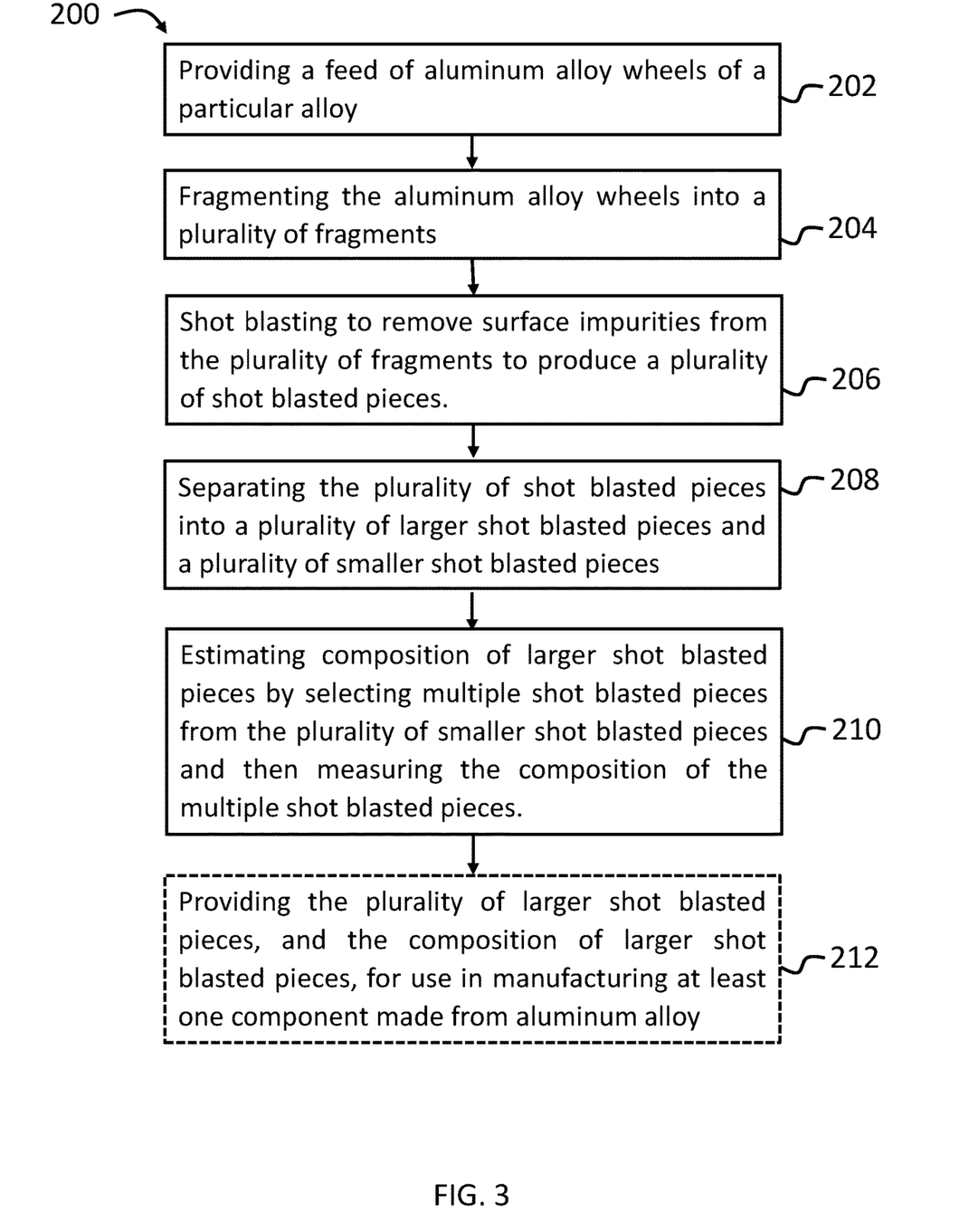
FIG. 3, in a flow chart, illustrates an alternative method of estimating a batch composition of a feed of aluminum alloy wheels for recycling of FIG. 2.

Referring now to FIG. 3, in some examples of method 200, the larger shot blasted pieces, together with an indication of the composition estimate of the smaller shot blasted pieces obtained in step 210, are provided for the use in manufacturing at least one component out of aluminum alloy. In some examples, in step 212, the larger shot blasted pieces, together with an indication of the composition estimate of the smaller shot blasted pieces obtained in step 210, are provided for the use in manufacturing at least one component out of A356.2 aluminum alloy. For example, a large sealed bag or sealed container containing the larger shot blasted pieces can be provided with the composition estimate, and possibly an uncertainty factor, written on the bag or container, or on a label affixed to the bag or container. In some examples, in step 212, the larger shot blasted pieces, together with an indication of the composition estimate of the smaller shot blasted pieces obtained in step 210, are provided for the use in manufacturing an aluminum alloy wheel. For example, a large sealed bag or sealed container containing the smaller shot blasted pieces can be provided with the composition estimate, and possibly an uncertainty factor, written on the bag or container, or on a label affixed to the bag or container. The container can be sealed to impede contamination during shipping so that the composition estimate, and uncertainty factor do not change significantly during shipping. The typical mass of such a container or bag might be over 1000 lbs. and 2000 lbs. and in some cases might be 2200 lbs. In some examples, the smaller shot blasted pieces are provided for recycling into a different component or components out of aluminum alloy than the larger shot blasted pieced. For example, the larger shot blasted pieces may be provided for recycling into components requiring higher value aluminum alloy. The smaller shot blasted pieces may be provided for recycling into components requiring only a lower value aluminum alloy.

Figure 4:
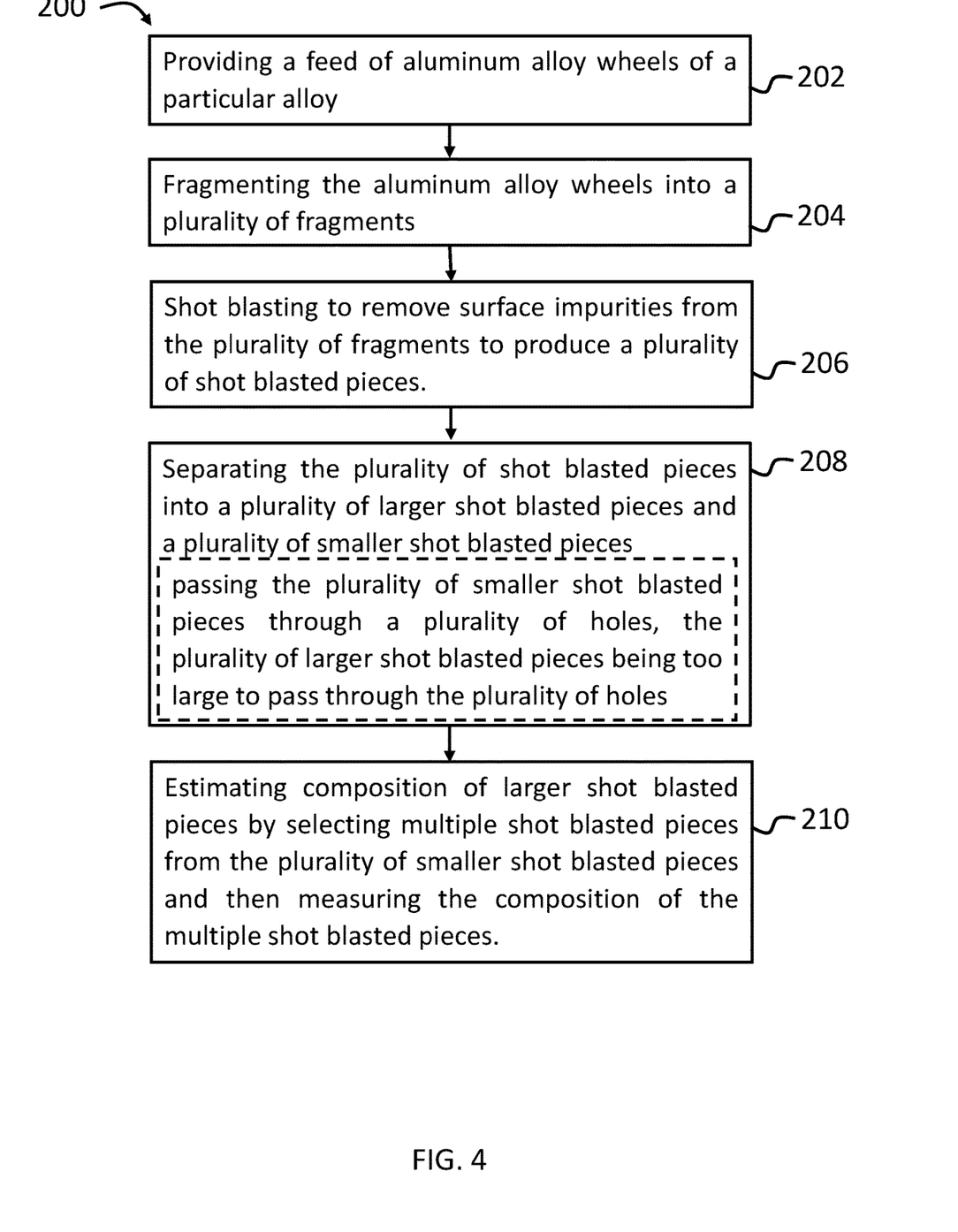
FIG. 4, in a flow chart, illustrates an alternative method of estimating a batch composition of a feed of aluminum alloy wheels for recycling of FIG. 2.

Referring now to FIG. 4, in some examples of step 208 of method 200, shot blasted pieces may be separated into a plurality of larger shot blasted pieces and a plurality of smaller shot blasted pieces by passing the smaller shot blasted pieces through a plurality of holes: the larger shot blasted pieces may be too large to pass through the plurality of holes. For example, the plurality of shot blasted pieces may be placed on a screen, mesh or grate. A certain number of these shot blasted pieces may fall or pass through the plurality of holes in the screen, mesh or grate, and be collected. The remainder of the shot blasted pieces may be large enough to prevent passage through the plurality of holes in the screen, mesh or grate. The shot blasted pieces that pass through the plurality of holes in screen mesh or grate are designated the smaller shot blasted pieces, while the shot blasted pieces that do not pass through the plurality of holes in the screen, mesh or grate are designated the larger shot blasted pieces: although, due to chance, the largest of the smaller shot blasted pieces may be larger than the smallest of the larger shot blasted pieces. For example, by chance, some smaller shot blasted pieces may not pass through the plurality of holes, while some larger shot blasted pieces may be shaped such that despite their relatively large size, they can and do pass through the plurality of holes. In some examples, the screen, mesh or grate may be in motion or vibrating to promote passage of shot blasted pieces through the plurality of holes in the screen, mesh or grate.

The holes in the screen, mesh or grate may be any shape, including but not limited to, circular, oval, square, or any other polygon. The holes on the screen mesh or grate may be any size. In some examples, the maximum breadth of each hole may be between half an inch and one inch.

Shot blasted pieces may be irregularly shaped. Due to this irregularity, pieces may only pass through the screen, mesh or grate at specific orientations. All other orientations may not allow shot blasted pieces to pass. This can also contribute to the largest of the smaller shot blasted pieces ending up being larger than the smallest of the larger shot blasted pieces.

Figure 5:
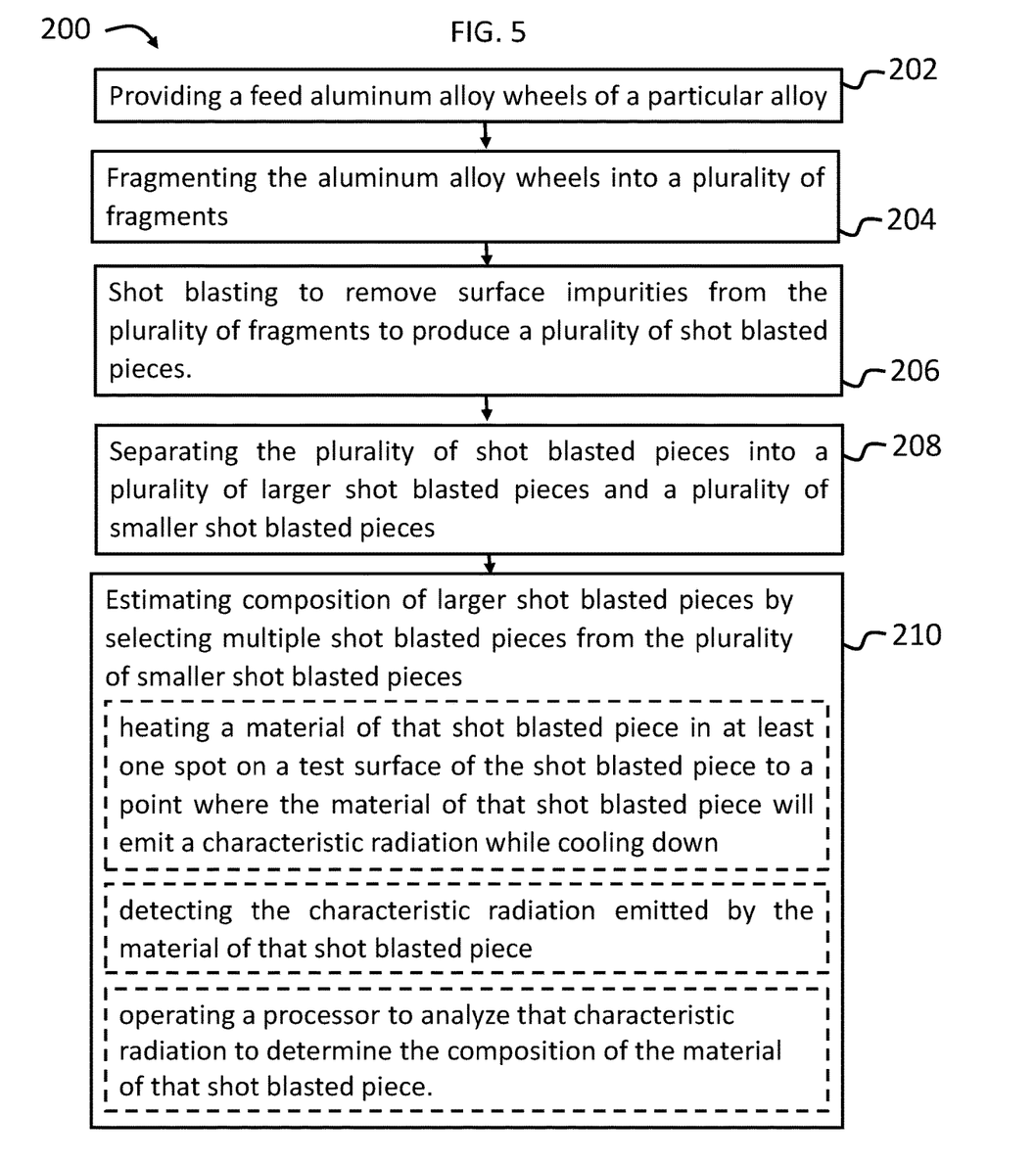
FIG. 5, in a flow chart, illustrates an alternative method of estimating a batch composition of a feed of aluminum alloy wheels for recycling of FIG. 2.

Referring now to FIG. 5, in some examples of step 210 of method 200, a laser scanner can be used to measure the composition of a plurality of smaller shot blasted pieces. This can involve using a laser to heat the material at a point on the surface of the shot blasted piece to a temperature at which that material will emit a characteristic radiation while cooling down. A sensor can then be operated to detect that characteristic radiation to provide a spectrum of signal magnitudes at different frequencies. This spectrum of signal magnitudes at different frequencies can then be analyzed by a computer processor to infer the relative concentrations of different elements within the alloy, as described, for example, in U.S. Pat. No. 10,220,418, incorporated herein by reference.

In one example of method 200, a "Laser-Induced Breakdown Spectroscopy" ("LIBS") composition analyzer manufactured by Laser Distance Spectrometry may be adapted as the laser scanner and sensor. The LIBS composition analyzer may include a radiation emitter, such as an Nd:YAG laser. The laser may shine at a frequency ranging from 1 to 20 hertz, thereby raising the temperature of the fragments at the point of contact between the shot blasted piece and the laser to above 30,000 degrees Celsius and generating plasma. The plasma may quickly cool down, returning the energized ions into a low energy state. While returning to the low energy state, the ions may emit characteristic radiation. The LIBS composition analyzer may contain one or more sensors that detect the characteristic radiation. A processor may then analyze readings obtained from the sensors and determine from them the concentration of the constituents contained in the material undergoing the temperature change. The processor may be disposed within the composition analyzer. Alternatively, the processor may be a remote processor.

Other suitable composition analyzers may include composition analyzers that use laser spectroscopy or other systems that rely on other methods of inducing characteristic radiation to be emitted by a material of each shot blasted piece at a surface of that shot blasted piece and detecting and analyzing that characteristic radiation to determine a composition of that material. The composition analyzers may detect the characteristic radiation by using any suitable sensor—for example, suitable sensors may include complementary metal-oxide-semiconductor (CMOS), high density, short channel metal-oxide-semiconductor (HMOS), charge-coupled device (CCD), and other types of sensors.

Suitable composition analyzers may use, for example, radiation emitters such as plasma, electron beam, or any other radiation emitters suitable to heat a material of each fragment in at least one spot on a surface of that fragment to a point where the material will emit a sufficient quantity and quality of characteristic radiation while cooling down so as to permit a sensor to detect that characteristic radiation and to allow for a processor to determine a composition of the material from that characteristic radiation. The composition analyzer can be adapted to withstand continuous use, as well as typical conditions that may be present in a particular aluminum alloy rim recycling operation. Such conditions may include vibrations resulting from the operation of aluminum alloy rim transfer mechanisms, and dust and other particles produced in the recycling process.

In some examples of step 210 of method 200, the measurement process includes providing the test surface of the shot blasted piece by removing layers of aluminum formerly covering the test surface to expose the test surface. Due to metallurgical effects such as elemental migration and corrosion, as previously mentioned, the surface composition of a shot blasted piece may not be representative of the interior composition of the shot blasted piece. By removing layers of aluminum covering the test surface of the smaller shot blasted pieces, a test surface may be exposed that provides a material sample characteristic of the internal composition of the shot blasted piece. The internal composition may more closely correspond to the aggregate composition of a piece, which may be the composition value of interest in terms of how the composition of an aluminum alloy product is likely to be affected by including that shot blasted piece in the batch used to produce the aluminum alloy product.

Figure 6:
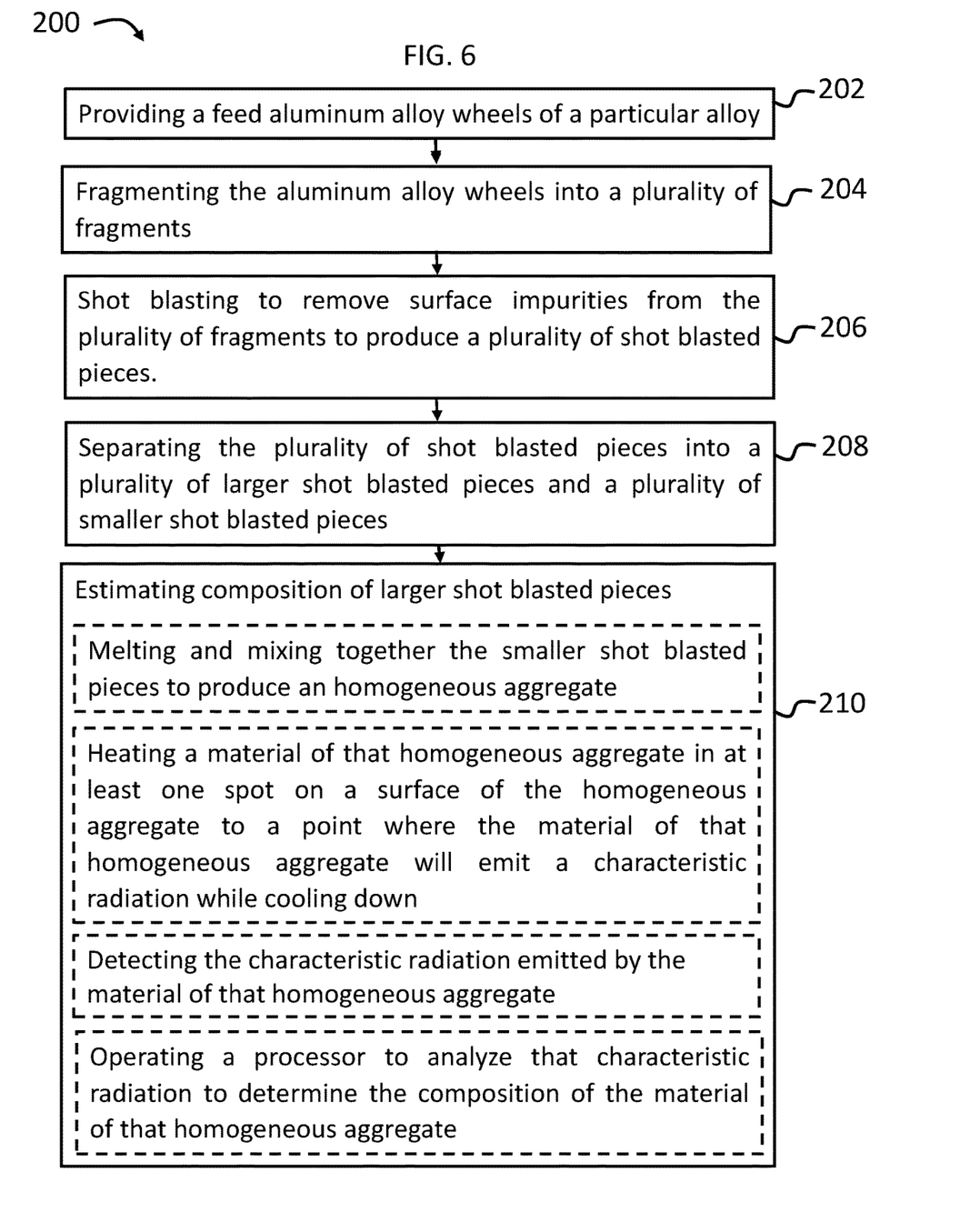
FIG. 6, in a flow chart, illustrates an alternative method of estimating a batch composition of a feed of aluminum alloy wheels for recycling of FIG. 2.

Referring now to FIG. 6, in some examples of step 210 of method 200, the smaller shot blasted pieces are provided and melted down to produce a homogeneous aggregate. This aggregate is then measured to determine elemental composition. The measurement method referred to at step 210 of FIG. 5 may be used to determine the composition of the homogeneous aggregate. This can involve heating the material at a point on the surface of the homogeneous aggregate using a laser to a temperature at which that material will emit a characteristic radiation while cooling down. A sensor can then be operated to detect that characteristic radiation to provide a spectrum of signal magnitudes at different frequencies. This spectrum of signal magnitudes at different frequencies can then be analyzed by a computer processor to infer the relative concentrations of different elements within the alloy.

The use of a homogeneous aggregate for composition testing at step 210 of method 200 can eliminate inconsistencies and variance in composition of shot blasted pieces. Due to metallurgical effects such as elemental migration and corrosion, as previously mentioned, the surface composition of a shot blasted piece may not be representative of the interior composition of the shot blasted piece. By melting down the smaller shot blasted pieces into a homogeneous aggregate, composition measurements can be made more representative of the average composition, without the variances caused by elemental migration. Also, different shot blasted pieces may have slightly different compositions, which can be averaged out by melting them down into the homogeneous aggregate. As previously mentioned, the composition of the homogeneous aggregate may be the most useful value when providing shot blasted pieces for recycling into new metal components.

This aggregate elemental composition can then be used to provide an estimate of the elemental composition of the larger shot blasted pieces. Statistical sampling methods may be used to provide this estimate, and an uncertainty value associated with this estimate.

Figure 7:
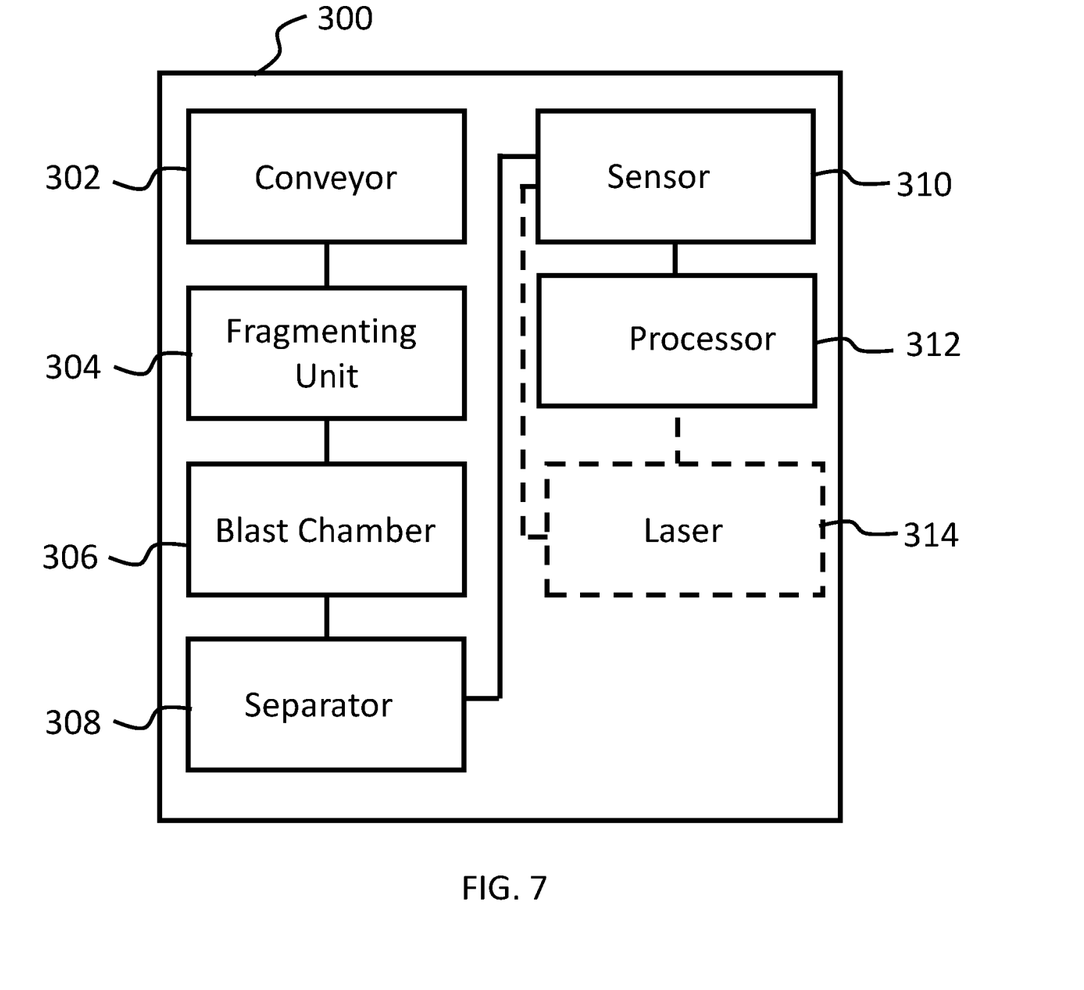
FIG. 7, is a block diagram showing a system for estimating a batch composition of waste metal pieces.

FIG. 7 shows a block diagram of a system 300 for recycling waste metal pieces. As shown, the system 300 for recycling waste metal pieces may include a conveyor 302, a fragmenting unit 304, a blast chamber 306, a separator 308 at least one sensor 310, and at least one processor 312. In some examples of system 300, there may also be a laser 314.

The conveyor 302 may provide a feed of waste metal pieces, such as, for example without limitation, aluminum alloy wheels, of a particular alloy. The waste metal pieces may be loaded onto the conveyor 302 by any suitable means (for example without limitation, by a truck dumping waste metal pieces into a hopper connected to one end of the conveyor 302 or manually by workers placing waste metal pieces on the conveyor).

In some examples of the system 300 for recycling waste metal pieces, the fragmenting unit 304 can receive the feed of waste metal pieces from the conveyor 302. The fragmenting unit 304 can fragment the waste metal pieces into a plurality of fragments. In some examples, the fragmenting unit may be a shredder or a cutter and a plurality of blades may be used to cut the waste metal pieces into a plurality of fragments. In other examples, the fragmenting unit may be a waterjet cutter.

The system 300 for recycling waste metal pieces includes a blast chamber 306. The blast chamber 306 can receive the feed of fragments from fragmenting unit 304. Within the blast chamber 306, abrasives such as shot may be projected against the fragments to clean their surfaces (shot blasting). The impact of the shot with these surfaces can remove coatings, corrosion, environmental contamination and debris from the surfaces. In some examples of the system 300, the blast chamber 300 may be a centrifugal blasting apparatus. One half inch or larger S330 steel shot can be used.

The centrifugal blasting apparatus may include a housing that completely encloses a conveying means formed of a plurality of flights extending crosswise between endless chains for travel along a predetermined path. This housing can be sectioned into four compartments including one entrance chamber, two blast chambers, and one shakeout chamber. The flights in the blast chambers can be made of blast-resistant manganese rods, while the flights in the shakeout and entrance chambers can be made of less expensive lighter duty material. The debris removed from the waste metal pieces can be removed from the system in the shakeout chamber, and the spent abrasive can be re-circled back to the blast wheel.

During the shot blasting process in the blast chamber 306, abrasives may impact fragments with sufficient energy to separate fragments into multiple, shot blasted pieces that are of smaller mass than the fragment from which they stem. The shot blasted pieces may be of varying sizes.

A feed of shot blasted pieces produced in the blast chamber 306 can be directed towards the separator 308. In some examples, the separator 308 may contain a plurality of holes. The holes may be in a mesh, grate or screen. A plurality of shot blasted pieces may be placed on a screen, mesh or grate. A certain number of shot blasted pieces may fall or pass through the plurality of holes in the screen, mesh or grate, and be collected. The remainder of the shot blasted pieces may be of a large enough size to prevent passage through the plurality of holes in screen, mesh or grate. The shot blasted pieces that pass through the screen mesh or grate can be designated smaller shot blasted pieces. The shot blasted pieces that do not pass through the plurality of holes in the screen, mesh or grate can be designated larger shot blasted pieces. In some examples, the screen, mesh or grate may be in motion or vibrating to promote passage of shot blasted pieces through the plurality of holes in the screen, mesh or grate.

In some examples, the maximum breadth of the holes in the mesh, grate or screen may be between half an inch and one inch.

In some examples, the fragmenting unit 304 can be configured relative to the separator 308 such that more than 95% of fragments produced in the fragmenting unit 304 may be too large to pass through the plurality of holes in the screen, mesh, or grate in the separator 308.

In some examples, the fragmenting unit 304 can be configured relative to the separator 308 such that more than 99% of fragments produced in the fragmenting unit 304 may be too large to pass through the plurality of holes in the screen, mesh, or grate in the separator 308.

The multiple shot blasted pieces can be selected from the group of smaller shot blasted pieces produced in the separator 308, and directed from the separator 308 toward at least one sensor 310. The at least one sensor 310 of the system 300 may be used to sense the plurality of shot blasted pieces produced by the blast chamber 306 to determine a plurality of composition measurements of the material of different shot blasted pieces in the plurality of smaller shot blasted pieces. As described above, in some examples of the system 300 the at least one sensor 310 may include a laser spectroscopy device.

The at least one processor 312 of the system 300 may be used to determine an aggregate composition measurement by measuring the composition of the material of a plurality of smaller shot blasted pieces. The at least one processor 312 may be linked for communication with the at least one sensor 310. The at least one processor 312 may be used to compute an estimate of the composition of the larger shot blasted pieces using i) the aggregate composition measurements obtained from the smaller shot blasted pieces and ii) statistical methods.

In some examples of system 300, a melting receptacle may be used to melt and mix a plurality of smaller shot blasted pieces into a homogenous aggregate. The melting receptacle may be, for example, a crucible. An aggregate composition measurement may be determined by measuring the composition of the homogenous aggregate. The at least one processor 312 may be linked for communication with the at least one sensor 310. The at least one processor 312 may be used to compute an estimate of the composition of the larger shot blasted pieces using i) the aggregate composition measurements obtained from the homogenous aggregate and ii) statistical methods.

In examples where the at least one sensor 310 includes a laser spectroscopy device, the system can also include a laser 314 for heating a portion the waste metal pieces to a point where the material will emit a characteristic radiation while cooling down. In this example, the laser spectroscopy device may measure that characteristic radiation and the laser spectroscopy device can be linked to the at least one processor 312 to analyze the characteristic radiation and to determine the composition measurements of the material. In some examples, the at least one processor 312 may include first and second processors. This first processor can analyze the spectrum and determine percentage compositions of various elements. The second processor may determine the aggregate batch composition. Alternatively, a single processor 312 may analyze the spectrum, determine percentage compositions of various elements, and then determine the aggregate batch composition.

The present invention has been described here by way of example only. Various modification and variations may be made to these exemplary embodiments without departing from the spirit and scope of the invention, which is limited only by the appended claims.

I claim:

1. A method of recycling aluminum alloy wheels, the method comprising:
   providing a feed of aluminum alloy wheels of a particular alloy;
   fragmenting a quantity of the aluminum alloy wheels into a plurality of fragments;
   subjecting the plurality of fragments to shot blasting to remove surface impurities from the plurality of fragments to produce a plurality of shot blasted pieces of the particular alloy;
   separating the plurality of shot blasted pieces into a plurality of larger shot blasted pieces of the particular alloy and a plurality of smaller shot blasted pieces of the particular alloy; and,
   providing the plurality of larger shot blasted pieces for use in producing a recycled aluminum alloy, without providing the plurality of smaller shot blasted pieces for use in producing that recycled aluminum alloy.

2. The method as defined in claim 1 wherein subjecting the pieces to shot blasting comprises producing most of the plurality of smaller shot blasted pieces.

3. The method as defined in claim 1 wherein producing most of the plurality of smaller shot blasted pieces comprises shot blasting the plurality of fragments to break most of the plurality of smaller shot blasted pieces off the plurality of fragments.

4. The method as defined in claim 1 further comprising providing the plurality of larger shot blasted pieces for use in manufacturing a component at least partly made of the recycled aluminum alloy from the larger shot blasted pieces.

5. The method as claimed in claim 4 wherein the component is an aluminum alloy wheel.

6. The method as defined in claim 4 wherein the recycled aluminum alloy is A356.2 aluminum alloy.

7. The method as defined in claim 4 further comprising collecting the smaller shot blasted pieces for use in producing a product different from the component made from the larger shot blasted pieces.

8. The method as defined in claim 1 wherein separating the plurality of shot blasted pieces into the plurality of larger shot blasted pieces and the plurality of smaller shot blasted pieces comprises passing the plurality of smaller shot blasted pieces through a plurality of holes, the plurality of larger shot blasted pieces being too large to pass through the plurality of holes.

9. The method as defined in claim 8 wherein a threshold maximum breadth of each hole in the plurality of holes is between half an inch and one inch.

10. The method as defined in claim 1 wherein more than 95% of a mass of the quantity of the aluminum alloy wheels is fragmented into fragments larger than the plurality of smaller shot blasted pieces.

11. The method as defined in claim 1 wherein more than 99% of a mass of the quantity of the aluminum alloy wheels is fragmented into fragments having a maximum length of greater than 1 inch.

12. The method as defined in claim 1 wherein more than 99% of a mass of the quantity of the aluminum alloy wheels is fragmented into fragments having a maximum length of between 1 inch and 8 inches.

13. The method as defined in claim 1 wherein providing the plurality of larger shot blasted pieces for use in producing the recycled aluminum alloy comprises sealingly containing the plurality of larger shot blasted pieces to isolate the plurality of larger shot blasted pieces from the smaller shot blasted pieces and from materials of substantially different composition to impede contamination of the plurality of the larger shot blasted pieces.

14. The method as defined in claim 8 wherein
fragmenting the quantity of the aluminum alloy wheels into the plurality of fragments comprises operating a plurality of shredders or cutters to shred or cut the aluminum alloy wheels into the plurality of fragments; and
the method further comprises configuring the plurality of shredders or cutters such that, in operation, more than 95% of a mass of the plurality of fragments is contained within fragments too large to pass through the plurality of holes.

15. The method as defined in claim 8 wherein
fragmenting the quantity of the aluminum alloy wheels into the plurality of fragments comprises operating a plurality of shredders or cutters to shred or cut the aluminum alloy wheels into the plurality of fragments; and
the method further comprises configuring the plurality of shredders or cutters such that, in operation, more than 99% of a mass of the plurality of fragments is contained within fragments too large to pass through the plurality of holes.

16. The method as defined in claim 1 wherein the surface impurities are surface coatings, corrosion, or environmental contamination.

17. The method as defined in claim 16 wherein the surface coatings are paints, metal electroplating, ceramic coatings or plastic coatings.

* * * * *